US012661381B2

(12) United States Patent
Bishawi et al.

(10) Patent No.: US 12,661,381 B2
(45) Date of Patent: Jun. 23, 2026

(54) METHODS FOR THE DELIVERY OF THERAPEUTIC AGENTS TO DONOR ORGANS

(71) Applicant: Duke University, Durham, NC (US)

(72) Inventors: Muath Bishawi, Durham, NC (US);
Carmelo Milano, Durham, NC (US);
Dawn Bowles, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 539 days.

(21) Appl. No.: 16/594,017

(22) Filed: Oct. 5, 2019

(65) Prior Publication Data

US 2020/0108109 A1     Apr. 9, 2020

Related U.S. Application Data

(60) Provisional application No. 62/741,689, filed on Oct. 5, 2018.

(51) Int. Cl.
| | |
|---|---|
| *C12N 15/864* | (2006.01) |
| *A01N 1/10* | (2025.01) |
| *A01N 1/126* | (2025.01) |
| *A61K 35/761* | (2015.01) |
| *C12N 15/113* | (2010.01) |
| *C12N 15/86* | (2006.01) |

(52) U.S. Cl.
CPC ............ *A61K 35/761* (2013.01); *A01N 1/126* (2025.01); *C12N 15/113* (2013.01); *C12N 15/86* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,593,130 B1 | 7/2003 | Sen et al. | |
| 8,465,970 B2 | 6/2013 | Hassanein et al. | |
| 10,076,112 B2 * | 9/2018 | Hassanein .............. | C12M 21/08 |
| 2006/0073127 A1 | 4/2006 | Kowalik et al. | |

FOREIGN PATENT DOCUMENTS

| | | | |
|---|---|---|---|
| WO | WO 2008112730 | * | 9/2008 |
| WO | WO 2018215571 | * | 11/2018 |

OTHER PUBLICATIONS

Shiraishi et al, Adenovirus-Mediated Gene Transfer Using Ex Vivo Perfusion of the Heart Graft, Jpn J Surg (1996) 26:624-628.*
Maxwell, Y.L. Many Hurdles to Clear Before Cardiac Xenotransplantation Takes Off. tctMD, 20022, pp. 1-4.*
Denner et al, Xenotransplantation—Progress and Problems: A Review, J Transplant Technol Res 2014, 4:2 , pag.*

Kivela et al, High Plasma Lipid Levels Reduce Efficacy of Adenovirus-Mediated Gene Therapy, Scientific Reports, 2017, pp. 1-8.*
Kossila et al, Improvement in Adenoviral Gene Transfer Efficiency after Preincubation at +378C in Vitro and in Vivo, Molecular Therapy, 2002, pp. 87-93.*
The TransMedics® Organ Care System (OCS™) Heart Technology Was Used to Perform The World's First Series of Adult Human Heart Transplants From Donors After Circulatory Death (DCD Donors) at St Vincent's Hospital, TransMedic publication, 2014, pp. 1-4.*
White et al., "Myocardial gene delivery using molecular cardiac surgery with recombinant adeno-associated virus vectors in vivo", Gene Therapy, 2011, vol. 18, 546-552.
Ardehali A, et al. (2015) Ex-vivo perfusion of donor hearts for human heart transplantation (PROCEED II): a prospective, open-label, multicentre, randomised non-inferiority trial. Lancet. 385:2577-2584.
Benjamin EJ, et al. (2017) Heart Disease and Stroke Statistics—2017 Update: A Report From the American Heart Association. Circulation. 135:e146-e603.
Grines CL, et al. (2003) A randomized, double-blind, placebo-controlled trial of Ad5FGF-4 gene therapy and its effect on myocardial perfusion in patients with stable angina. J Am Coll Cardiol. 42:1339-1347.
Harvey BG, et al. (1999) Variability of human systemic humoral immune responses to adenovirus gene transfer vectors administered to different organs. J Virol. 73:6729-6742.
Kadner A, et al. (2000) Heterotopic heart transplantation: experimental development and clinical experience. Eur J Cardiothorac Surg. 17:474-481.
Katz MG, et al. (2016) Gene Therapy in Cardiac Surgery: Clinical Trials, Challenges, and Perspectives. Ann Thorac Surg. 101:2407-2416.
Matkar PN, et al (2016) Cardiac gene therapy: are we there yet? Gene Ther. 23:635-648.
Messina EL, et al. (2012) Adeno-associated viral vectors based on serotype 3b use components of the fibroblast growth factor receptor signaling complex for efficient transduction. Hum Gene Ther. 23(10):1031-1042.
Miyagi N, et al. (2008) Efficient and durable gene transfer to transplanted heart using adeno-associated virus 9 vector. J Heart Lung Transplant. 27:554-560.
Pellegrini C, et al. (1998) Influence of temperature on adenovirus-mediated gene transfer. Eur J Cardiothorac Surg 13:599-603.
Piacentino V3rd, et al. (2012) X-linked inhibitor of apoptosis protein-mediated attenuation of apoptosis, using a novel cardiac-enhanced adeno-associated viral vector. Hum Gene Ther. 23:635-646.
Schechter, MA, et al. (2014) An isolated working heart system for large animal models. J Vis Exp. 88:51671.

(Continued)

*Primary Examiner* — Maria Marvich
(74) *Attorney, Agent, or Firm* — Polsinelli PC

(57) ABSTRACT

The present invention relates to methods of administering therapeutic agents to a donor organ prior to transplant comprising circulating the therapeutic agent through the donor organ while maintaining the donor organ under ex vivo perfusion conditions, as well as methods of transplanting organs, biologically modifying a donor organ prior to transplant, and treating organ failure using the methods disclosed herein.

12 Claims, 5 Drawing Sheets

Specification includes a Sequence Listing.

(56)            References Cited

OTHER PUBLICATIONS

Shah AS, et al. (2000) Adenovirus-mediated genetic manipulation of the myocardial β-adrenergic signaling system in transplanted hearts. The Journal of Thoracic and Cardiovascular Surgery. 120:581-588.

Stamp NL, et al. (2015) Successful Heart Transplant after Ten Hours Out-of-body Time using the TransMedics Organ Care System. Heart Lung Circ. 24:611-613.

Stehlik J, et al. (2018) Honoring 50 Years of Clinical Heart Transplantation in Circulation: In-Depth State-of-the-Art Review. Circulation. 137(1):71-87.

Stewart DJ, et al. (2006) Angiogenic gene therapy in patients with nonrevascularizable ischemic heart disease: a phase 2 randomized, controlled trial of AdVEGF(121) (AdVEGF121) versus maximum medical treatment. Gene Ther. 13:1503-1511.

Smith AC, et al. (2006) Preparation of swine for the laboratory. ILAR J. 47(4):358-363.

* cited by examiner

1

METHODS FOR THE DELIVERY OF THERAPEUTIC AGENTS TO DONOR ORGANS

CROSS REFERENCE TO RELATED APPLICATIONS

This application claims priority to U.S. Provisional Patent Application Ser. No. 62/741,689, filed Oct. 5, 2018, the contents of which are hereby incorporated by reference in their entirety.

BACKGROUND OF THE INVENTION

INCORPORATION BY REFERENCE OF SEQUENCE LISTING PROVIDED ELECTRONICALLY

This application contains a Sequence Listing submitted on 5 Oct. 2019 as an electronic.txt file named "19-1835-US_SeqList", having a size of 4096 bytes and created on 5 Oct. 2019. The information contained in this electronic.txt file is incorporated herein by reference in its entirety.

Field of the Invention

The present invention relates to methods of administering therapeutic agents to a donor organ prior to transplant comprising circulating the therapeutic agent through the donor organ while maintaining the donor organ under ex vivo perfusion conditions, as well as methods of transplanting organs, biologically modifying a donor organ prior to transplant, and treating organ failure using the methods disclosed herein.

Description of the Related Art

Cardiovascular diseases (CVD) remain the leading cause of death worldwide. The number of CVD patients with heart failure (HF) in the US is approaching 6.5 million adults and is estimated to increase by 46% in the next decade so that there will be more than 8 million adults in the US with HF by 2030 (Benjamin, E. J. et al. Heart Disease and Stroke Statistics-2017 Update: A Report From the American Heart Association. *Circulation* 135, e146-e603, doi:10.1161/CIR.0000000000000485 (2017)). HF has no cure and about 50% of people who develop HF die within five years of diagnosis. Once a patient develops end stage heart failure, therapeutic options are limited to palliative care, some type of mechanical circulatory support, or cardiac transplantation. While cardiac transplantation remains the gold standard therapy for qualifying patients, it is still limited by the supply of organs, and fraught with post-transplant complications such as graft dysfunction, allograft vasculopathy, rejection, and the side effects of immunosuppression (Stehlik, J., Kobashigawa, J., Hunt, S. A., Reichenspurner, H. & Kirklin, J. K. Honoring 50 Years of Clinical Heart Transplantation in Circulation: In-Depth State-of-the-Art Review. *Circulation* 137, 71-87, doi:10.1161/CIRCULATION-AHA.117.029753 (2018)). There continues to be a need for improvement in cardiac transplantation, and gene therapy approaches may be able to address some of the post-transplant complications.

A successful gene therapy approach based on viral vectors requires three elements: delivery vehicle (a capsid shell), a therapeutic target (a transgene) and a physical method of delivery into the tissue(s) of interest (direction injection, intravenous (IV) administration, etc.) (Matkar, P. N., Leong-Poi, H. & Singh, K. K. Cardiac gene therapy: are we there yet? *Gene Ther* 23, 635-648, doi:10.1038/gt.2016.43 (2016)). Preclinical and clinical data strongly support the importance of route of delivery for efficacy and safety of viral vector transduction of the heart (Id.). Early clinical trials utilized surgical thoracotomy and direct viral vector injections into the myocardium (Stewart, D. J. et al. Angiogenic gene therapy in patients with nonrevascularizable ischemic heart disease: a phase 2 randomized, controlled trial of AdVEGF(121) (AdVEGF121) versus maximum medical treatment. *Gene Ther* 13, 1503-1511, doi:10.1038/sj.gt.3302802 (2006)). This approach achieved significant local transgene expression but even with multiple injections, the majority of the myocardium for a human size heart cannot be affected. Additional delivery techniques included catheter-based delivery to the endocardium (Grines, C. L. et al. A randomized, double-blind, placebo-controlled trial of Ad5FGF-4 gene therapy and its effect on myocardial perfusion in patients with stable angina. *J Am Coll Cardiol* 42, 1339-1347 (2003)). Perhaps most promising was vector delivery via repeated catheter based intracoronary injections, however, without full cardiac isolation on cardiopulmonary bypass, significant viral vector reaches secondary organs. In fact, a recent large-scale review of gene therapy clinical trials for cardiac disease concluded that present delivery approaches (intracoronary or intravenous administration) might not deliver sufficient amounts of the vector to the target tissue (Katz, M. G., Fargnoli, A. S., Kendle, A. P., Hajjar, R. J. & Bridges, C. R. Gene Therapy in Cardiac Surgery: Clinical Trials, Challenges, and Perspectives. *Ann Thorac Surg* 101, 2407-2416, doi:10.1016/j.athoracsur.2015.12.004 (2016)).

Proof of concept of the benefit of gene therapy in the context of heart transplant to ameliorate deleterious responses to the graft in the recipient has been demonstrated in rodent heart transplant models using cold static storage or Langendorff delivery methods (Shah, A. S. et al. Adenovirus-mediated genetic manipulation of the myocardial β-adrenergic signaling system in transplanted hearts. *The Journal of Thoracic and Cardiovascular Surgery* 120, 581-588, doi:10.1067/mtc.2000.107519 (2000); Miyagi, N. et al. Efficient and durable gene transfer to transplanted hearts using adeno-associated virus 9 vector. *J Heart Lung Transplant* 27, 554-560, doi:10.1016/j.healun.2008.01.025 (2008)). Of the two delivery approaches, it is unlikely that standard of care organ storage (cold static storage) will facilitate translation of gene therapy for transplantation since many aspects of the viral vector transduction process such as receptor entry, uptake, trafficking through the cell, nuclear import, and efficient disassembly are temperature and metabolism dependent (Pellegrini, C. et al. Influence of temperature on adenovirus-mediated gene transfer. *Eur J Cardiothorac Surg* 13, 599-603 (1998)). Shah et al reported first that viral vectors could be delivered to an explanted rat heart ex vivo during the preservation period, thus increasing the time during which the vector is present in the vasculature (Shah, A. S. et al. Adenovirus-mediated genetic manipulation of the myocardial β-adrenergic signaling system in transplanted hearts. *The Journal of Thoracic and Cardiovascular Surgery* 120, 581-588, doi:10.1067/mtc.2000.107519 (2000)). However, vectors given into the coronary circulation prior to cold static storage achieved limited transgene expression. Limited transgene expression in this model probably resulted from lack of metabolic activity required for vector attachment to receptors and cellular uptake, with washout of the vector occurring during warm reperfusion.

Isolated perfusion systems such as a Langendorff have been utilized experimentally for over 90 years in physiologi- cal and pharmacological research to evaluate cardiac func- tion ex vivo (Schechter, M. A. et al. An isolated working heart system for large animal models. *J Vis Exp*, doi: 10.3791/51671 (2014)). These perfusion strategies maintain normothermic and aerobic metabolism, facilitating the bio- chemical and molecular steps necessary for viral uptake into the heart.

Several companies have developed ex vivo perfusion systems intended to mitigate ischemic injury during organ preservation. Clinically, these devices may replace the cold static storage preservation strategy for solid organ trans- plant. An ex vivo warm blood perfusion system (The Organ Care System (OCS™) TransMedics Inc., Andover MA) has been the most clinically tested device for cardiac transplan- tation (Ardehali, A. et al. Ex-vivo perfusion of donor hearts for human heart transplantation (PROCEED II): a prospec- tive, open-label, multicentre, randomised non-inferiority trial. *Lancet* 385, 2577-2584, doi:10.1016/S0140-6736(15) 60261-6 (2015)). This device is portable and is primed with heparinized donor blood mixed with a proprietary perfusion solution. Once on the device, the heart is maintained in a nonworking but metabolically active mode. This device has achieved successful clinical ex vivo perfusion for prolonged periods of time (Stamp, N. L. et al. Successful Heart Transplant after Ten Hours Out-of-body Time using the TransMedics Organ Care System. *Heart Lung Circ* 24, 611-613, doi:10.1016/j.hlc.2015.01.005 (2015)). While the main goal of perfusion storage is to reduce ischemia reper- fusion injury, improve the safety, and extend the time of the preservation phase, perfusion storage uniquely isolates the metabolically active cardiac graft, and potentially enables biological modification. Thus, the inventors envisaged that this type of perfusion storage might allow for successful gene therapy by way of intracoronary delivery of high concentrations of viral vectors with continuous recirculation under metabolically favorable conditions.

SUMMARY OF THE INVENTION

In one aspect, the invention provides a method of admin- istering a therapeutic agent to a donor organ prior to trans- plant comprising circulating the therapeutic agent through the donor organ while maintaining the donor organ under ex vivo perfusion conditions.

In a second aspect, the invention provides a method of transplanting an organ into a subject in need of an organ transplant comprising administering a therapeutic agent to a donor organ prior to transplant comprising circulating the therapeutic agent through the donor organ while maintaining the donor organ under ex vivo perfusion conditions, and subsequently transplanting the donor organ into the subject.

In a third aspect, the invention provides a method of modifying a donor organ prior to transplantation comprising administering a therapeutic agent to the donor organ and circulating the therapeutic agent through the donor organ while maintaining the donor organ under ex vivo perfusion conditions.

In a further aspect, the invention provides a method of treating organ failure in a subject comprising transplanting a donor organ into the subject, wherein a therapeutic agent has been administered to the donor organ prior to transplan- tation by a method comprising circulating the therapeutic agent through the donor organ while maintaining the donor organ under ex vivo perfusion conditions.

BRIEF DESCRIPTION OF THE DRAWINGS

FIG. 1A. Influence of OCS solution. 1000 particles Ad luciferase per Hela cell were mixed with media and increasing percentage of OCS solution and used to infect Hela cells. RLU were determined 24 hours post infection. Data is shown fold change in RLU compared to untransduced Hela cells. FIG. 1B. Influence of whole blood. Same as FIG. 1A except OCS solution was mixed with whole porcine blood. FIG. 1C. Influence of blood components. Cell based luminescence assay to mea- sure Ad Luciferase transduction efficiency with OCS solu- tion and pig blood components. FIG. 1D. Influence of OCS circuitry. Viral transduction efficiency over time while on the circuit with a heart. OCS circuit was set up with washed donor pig blood, Ad Luciferase and the donor heart. (RLU=relative light units)

FIG. 3A. Lane 1, Native LV; Lane 2, Native RV; Lane 3, Liver; Lane 4; Native Septum; Lane 5, Allograft LV; Lane 6, Allograft RV; Lane 7, Allograft Septum; Lane 8, Naïve pig LV. FIG. 3B. Luciferase activity from tissues corresponding to lanes 1-8 in FIG. 3A.

DETAILED DESCRIPTION OF THE INVENTION

Figure 1A:
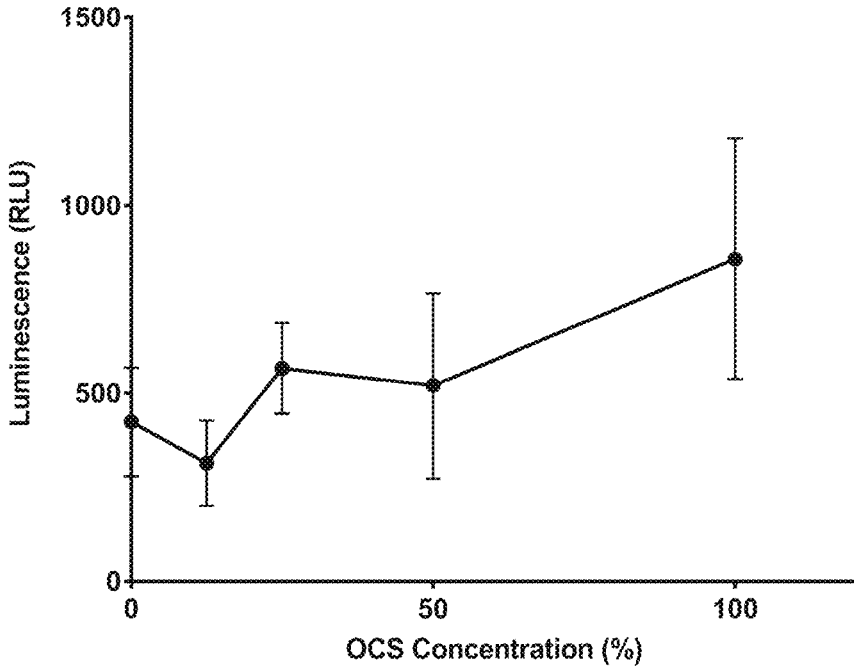
FIGS. 1A-1D. Cell based assessment of OCS components on viral vector transduction efficiency.

For the purposes of promoting an understanding of the principles of the present disclosure, reference will now be made to particular embodiments of the invention and spe- cific language will be used to describe the same. It will nevertheless be understood that no limitation of the scope of the disclosure is thereby intended, such alteration and fur- ther modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also con- templated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

The inventors have discovered that therapeutic agents can be successfully administered to a donor organ prior to transplant under ex vivo perfusion conditions. In particular, robust and diffuse transduction from a viral vector can be achieved in an allograft using an ex vivo organ perfusion strategy to deliver the viral vector prior to transplantation, allowing for delivery of a therapeutic agent prior to transplantation. "Donor organ" and "allograft" are used interchangeably herein.

The methods disclosed herein may be used in instances where a donor organ is suitably matched and appropriate for transplantation, and in such instances the donor organ may be modified prior to transplantation through the administration of a therapeutic agent in accordance with the methods herein to, inter alia, improve the clinical outcome of transplantation, for example to mitigate graft dysfunction, allograft vasculopathy, rejection, or side effects from immunosuppression. The methods disclosed herein may also be used with marginal organs, high risk organs, or otherwise non-transplantable organs, e.g. unusable, non-compatible, and/or immunologically mismatched organs, to modify such organs with a therapeutic agent so that they are better suited for transplantation or may be used for transplantation. The methods herein may also be used to modify an organ such that it could be used for a purpose other than transplantation, or to allow the organ to be stored prior to transplantation.

Accordingly, in a first aspect, the present invention provides a method of administering a therapeutic agent to a donor organ prior to transplant comprising circulating the therapeutic agent through the donor organ while maintaining the donor organ under ex vivo perfusion conditions. As used herein, a "therapeutic agent" is any molecule that can be used for treatment or therapy as defined herein, and encompasses both the molecule administered and any product thereof (e.g. a viral vector comprising a transgene as well as the protein produced by expression of the transgene). Exemplary therapeutic agents include, but are not limited to, stem cells and other cellular therapies, nucleic acids, proteins, and other biopolymers, cellular organelles, and small molecule therapeutics. In certain embodiments of the invention the therapeutic agent is a biologic, including, but not limited to, a vector comprising a transgene, allowing for the delivery of therapeutic agents by way of gene therapy.

The vector may be non-viral or viral. In certain embodiments, the vector is a viral vector. In other embodiments, the vector is a pseudotyped viral vector. In some embodiments, the viral vector is an adenoviral vector, a retroviral vector, an adeno-associated viral vector, a lentoviral vector, a pox viral vector, and alphaviral vector, or a herpes viral vector. In certain embodiments, the viral vector is an adenoviral vector (including, but not limited to, an adenoviral serotype 5 vector) or an adeno-associated viral vector. The viral vector may comprise any suitable promotor, e.g. constitutive expressing or inducible promoters, or general or cell specific promoters. In some embodiments, the viral vector comprises a CMV promotor.

Selection of an appropriate viral vector is within the purview of one of skill in the art. Use of an adenoviral (Ad) vector may offer robust early-onset gene expression and the benefit of a large DNA packaging capacity, and would be suitable for treatments requiring short-term limited gene expression. This may include, for example, genes aimed at increasing early inotrope of the heart during the early post-operative period, without the risk of arrhythmias, hypertrophy or heart failure associated with long term expression. Use of an adeno associated virus (AAV) may offer the benefit of long-term gene expression in the allograft and less immunogenicity than Ad vectors (Postrach, J. et al. Adeno-associated viral vector 2.9 thymosin ss4 application attenuates rejection after heart transplantation: results of a preclinical study in the pig. *Transplantation* 98, 835-843, doi:10.1097/TP.0000000000000327 (2014)). AAV based vectors would be suitable for therapies using genes targeted at suppressing the immune response against the allograft where long-term, sustained gene expression would be desired.

The transgene may be any gene that will improve the outcome of transplant of the donor organ, and may be endogenous or exogenous. Exemplary transgenes include, but are not limited to, those that improve the organ's function (such as positive inotropic genes, e.g. those that increase beta-receptor expression or types), decrease ischemic reperfusion injury (such as increasing ROS scavenging enzymes), decrease immunogenicity (such as knocking out HLA system or increasing expressing of anti-inflammatory molecules such as IL-10), allow for an incompatible organ or xenotransplantation to be transplanted, or a combination thereof.

In some embodiments, the transgene is expressed at a level such that there is an increase in the abundance, activity, and/or downstream biological effect, as applicable, of the expressed protein up to 1000×, e.g. an increase of about 10×, about 100×, about 200×, about 300×, about 500×, or about 1000× relative to baseline (i.e. absent the transgene). An increase may range from 5% to 1000×. Similarly, an increase in the abundance, activity, and/or downstream biological effect, as applicable, may be about 5% or more, e.g. an about 10%, 20%, 30%, 40%, 50%, 60%, 70%, 80%, or 90% increase relative to baseline. Alternatively there may be, as applicable, a decrease in abundance, activity, and/or downstream biological effect down to 0x relative to baseline. There may be a decrease of about 5% or more, e.g. an about 10%, 20%, 30%, 40%, 50%, 60%, 70%, 80%, or 90% decrease.

In certain embodiments, the viral vector is administered at a load of or of about $1\times10^8$ to $1\times10^{15}$ total viral particles per organ, or any range or level within this range. For example, in some embodiments, the viral vector is administered at a load of or of about $1\times10^{10}$ to $1\times10^{14}$, $1\times10^{11}$ to $1\times10^{14}$, $1\times10^{12}$ to $1\times10^{14}$, $1\times10^{13}$ to $1\times10^{14}$, $1\times10^{10}$ to $1\times10^{15}$, $1\times10^{11}$ to $1\times10^{15}$, $1\times10^{12}$ to $1\times10^{15}$, or $1\times10^{13}$ to $1\times10^{15}$ total viral particles per organ, or at a load of or of about $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, $1\times10^{13}$, $5\times10^{13}$, $1\times10^{14}$, $5\times10^{14}$, $1\times10^{15}$, $5\times10^{15}$ total viral particles per organ. In some embodiments, the viral vector is administered at a load of about $5\times10^{13}$ or more total viral particles per organ.

In the methods of the invention, the donor organ may be a mammalian organ, including but not limited to a human organ. In some embodiments, the donor organ is a kidney, a liver, a lung, or a heart. In certain embodiments, the organ is a heart. In the methods of the invention, the organ, e.g. heart, may be maintained in a nonworking but metabolically active state while under perfusion conditions.

The ex vivo perfusion conditions of the methods of the invention may be maintained by any device that provides one or more of: i) complete or partial isolation of the organ of interest, ii) normothermia or intermittent normothermia, and iii) recirculation. Accordingly, in non-limiting examples, the ex vivo perfusion conditions may be maintained using a Langendorff perfusion system, a warm blood perfusion system, a cold storage system with intermittent perfusion, or any other perfusion system that maintains the organ, at least in part, in a state conducive to uptake of the therapeutic agent into the organ and, as applicable, expression of the transgene contained therein. One of skill in the art will be able to select appropriate ex vivo perfusion conditions for the particular therapeutic agent administered. In a non-limiting example, a cold perfusion recirculating system may a suitable option for use with small molecule therapeutic agents. In certain embodiments, the ex vivo perfusion conditions are normothermic ex vivo perfusion conditions, which may be used in instances where the successful administration of the therapeutic agent is dependent upon temperature and/or metabolism of the donor organ, e.g. in certain instances where viral vectors are used for gene therapy. Exemplary warm blood perfusion systems include, but are not limited to, the Organ Care System™ (OCS).

The methods recited above may be performed by: (a) harvesting the donor organ and optionally blood from the donor; (b) priming the ex vivo perfusion circuit with a perfusion solution mixture; (c) adding the therapeutic agent to the ex vivo perfusion circuit and placing the organ on the ex vivo perfusion device; and (d) perfusing the organ.

The perfusion solution mixture may be any combination of a perfusion solution and one or more additional components, where the additional component(s) may be a donor blood product or any suitable alternative thereto, including non-cellular solutions. Alternatively, the perfusion solution mixture may be a perfusion solution alone, or mixture of more than one perfusion solution. Exemplary alternatives to a donor blood product include, but are not limited to, blood from an alternate source (e.g. from a blood bank), non-blood based perfusion solutions, perfluorocarbons, hemoglobin-based solutions, and blood replacement solutions. The perfusion solution may be any suitable solution used in the art. In certain embodiments where the OCS is utilized, the perfusion solution may be the proprietary perfusion solution of the manufacturer.

The donor blood product may be whole blood from the allograft donor, or one or more isolated components thereof, optionally mixed with additional substances not native to the donor. Accordingly, the blood may be treated to selectively remove or inactivate, in whole or in part, undesirable components, including, e.g., antibodies that inhibit vector expression. Such treatments include, but are not limited to, blood washing, plasmapheresis, and antibody filters, as well as the addition of agents that bind antibodies. In certain embodiments, the treatment results in a reduction in the presence of or activity of the target component(s) by 5% to 90%, or by any range or value within this range, such as by 5% to 80%, by 10% to 80%, by 20% to 70%, by 30% to 70%, by 10% to 60%, by 20% to 70%, by 50% to 80%, by 60% to 80%, or by 70% to 90%, or by 5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, or 90% or more. The inventors have found that in certain instances, the plasma and serum of the donor blood may interfere with the transduction process of the transgene of the therapeutic agent leading to diminished expression of the transgene target. Accordingly, in some embodiments, the donor blood may be washed or otherwise treated such that the blood is partially or substantially free of plasma and serum. As used herein "substantially free" means less than about 10% of the component remains. In a non-limiting example, the blood may be washed using a blood salvage device. Following treatment, the red blood cells may be reconstituted to form a solution with an osmotic pressure substantially the same as that of whole blood.

The addition of the therapeutic agent to the ex vivo perfusion circuit and the placement of the organ on the ex vivo perfusion device can be done in any order, or concurrently. Any reference to these in combination is not meant to imply any particular timing of one relative to another unless otherwise clearly indicated. Accordingly, the therapeutic agent may be added to the ex vivo perfusion circuit and the organ subsequently placed on the ex vivo perfusion device, the organ may be placed on the ex vivo perfusion device and the therapeutic agent subsequently added to the ex vivo perfusion device, or the therapeutic agent may be added to the ex vivo perfusion device at the same time as the organ is placed on the ex vivo perfusion device. In certain instances, the therapeutic agent may be added to the perfusion circuit at a location near the organ to assist with uptake of the therapeutic agent.

The organ may be perfused for any suitable length of time, such as any time period from about 3 minutes to about 9 hours, or any range or time within this range. In certain embodiments, the organ is perfused for about 5 minutes to about 6 hours, from about 15 minutes to about 3 hours, or from about 1 hour to about 2 hours. In other embodiments, the organ may be perfused for 3 minutes, 5 minutes, 15 minutes, 30 minutes, 1 hour, 2 hours, 3 hours, 5 hours, or 9 hours. In certain embodiments, the organ may be perfused for 2 hours or longer as needed. Repeated circulation of the viral vector increases time for viral vector interaction with cell surface primary and secondary receptors and may result in diffuse robust expression of the transgene in the allograft.

In a further aspect, the invention provides a method of transplanting an organ into a subject in need of an organ transplant comprising administering a therapeutic agent to a donor organ according to the methods described above and subsequently transplanting the donor organ into the subject. In certain embodiments, the subject is a mammal, and in some embodiments the subject is a human.

The inventors have found that in certain instances, transgene expression was highly elevated in all parts of the allograft without detectable expression in any of the other organs of the recipient. Accordingly, in certain embodiments, following transplant, the activity of the protein encoded by the transgene is limited to the transplanted organ. Lack of off-target delivery provides certain benefits, including, but not limited to, the reduction or elimination of adverse side effects, such as the expression of the transgene in other organs. Additionally non-specific inflammatory system activation may be avoided or reduced.

In a third aspect, the invention provides a method of modifying a donor organ prior to transplantation comprising administering a therapeutic agent to the donor organ and circulating the therapeutic agent through the donor organ while maintaining the donor organ under ex vivo perfusion conditions in accordance with the methods described above. In certain embodiments of this aspect of the invention, the donor organ is modified to mitigate graft dysfunction, allograft vasculopathy, rejection, or side effects from immunosuppression.

In a fourth aspect, the invention provides a method of treating organ failure in a subject comprising transplanting a donor organ into the subject, wherein a therapeutic agent has been administered to the donor organ prior to transplantation by a method comprising circulating the therapeutic agent through the donor organ while maintaining the donor organ under ex vivo perfusion conditions in accordance with the methods described above. In certain embodiments of this aspect of the invention, the organ failure is heart failure and the donor organ is a donor heart.

EXAMPLES

Example 1: Methods

Animals

Outbred Yorkshire pigs (females of approximate weight of 30-35 kg) were used in this study. All work in this report has been approved by Duke University Institutional Animal Care and Use Committee. All experiments were performed in accordance with relevant guidelines and regulations. Transplant and recipient pig were littermates of compatible blood types.

Recombinant Adenoviral Vector

The adenoviral (Ad) luciferase vector (serotype 5) was obtained from the Pittsburgh Human Gene Therapy Center (Pittsburgh, PA) and was used previously (Piacentino, V., 3rd et al. X-linked inhibitor of apoptosis protein-mediated attenuation of apoptosis, using a novel cardiac-enhanced adeno-associated viral vector. *Hum Gene Ther* 23, 635-646, doi:10.1089/hum.2011.186 (2012)).

Cell Based Luminometer Assays

Luminometry (either cell or tissue-based) was performed with a Veritas luminometer (Turner Biosystems, Sunnyvale, CA). HeLa cells were plated at 10,000 cells per well in 96-well plates. The cells were infected with 1000 particles/cell of Ad-CMV luciferase in the presence of normal growth media (DMEM, 10% FBS) and additional test additives including OCS solution, whole blood, plasma, and serum. 24 hours post infection, the 96-well plates were processed and light emission per well was determined as described previously in Messina et al. (Messina, E. L. et al. Adeno-associated viral vectors based on serotype 3b use components of the fibroblast growth factor receptor signaling complex for efficient transduction. *Hum Gene Ther* 23, 1031-1042, doi:10.1089/hum.2012.066 (2012)).

Example 2: Viral Vector Delivery and Heart Transplantation

The donor heart was procured in a standard fashion with modifications described below specific to OCS perfusion. Heparin was administered (300 U/kg/IV), and approximately 1-1.3 liter of blood was drained directly from the right atrium prior to cross clamp. After cross clamping the ascending aorta, 500 ml cold del Nido cardioplegia (plasmalyte A, pH 7.4 (994 ml); Mannitol, 25% (13 ml); Magnesium Sulfate, 50% (4 ml); Sodium bicarbonate, 1 mEq ml, (13 ml); potassium chloride, 2 mEq/ml (13 ml); sterile water for injection (3 ml); Lidocaine HCL 2% (6.5 ml); mixed at Duke Compounding Facility) was delivered into the aortic root to arrest the heart. The heart was excised and prepared for the OCS device. The superior and inferior vena cavae were over-sewn; the ascending aorta was cannulated to serve as perfusion inflow, while the main pulmonary artery was cannulated to collect the heart's venous drainage. The pulmonary veins and left atrium were left open and a vent was placed through one of the veins, across the mitral valve in the LV. Ventricular pacing leads were placed to maintain a rate of at least 80 beats per minute. Concurrently, the 1-1.3 liters of donor pig blood which was acquired at the time of organ harvest was diluted 1:1 with Plasma Lyte A (Baxter HealthCare Corporation) in reservoir and washed with 1 L physiological solution using a 250 ml Brat 2 bowl and a CellSaver (Brat 2) Autologous Blood Recovery System (Haemonetics, Braintree, MA).

Preparation of the perfusion solution deviated from the standard OCS protocol in three aspects: a) blood washing described above, b) adjustment of blood cell/OCS solution mixture and c) addition of $5 \times 10^{13}$ total viral particles of Adenoviral CMV-luciferase vector (Ad CMV-luc). First, the washed red blood cell fraction was reconstituted with the components shown in Table 1 then $5 \times 10^{13}$ Ad CMV-luc was added to the mixture. Following a 5-15 minute priming of the circuit with this mixture (same time needed for preparing the heart for the OCS ~20 minutes), the heart was added to the device and maintained for 2 hours. Target mean perfusion pressure was 65-70 mmHg, and target coronary flow rate was 600 ml per minute. Samples of the blood/OCS/viral vector mixture were acquired during the initial set-up, pump priming, and at 15-30 minutes intervals during the perfusion run for study.

TABLE 1

| Composition of perfusate for OCS machine. Final volume of the circuit was 1626 ml. | |
| --- | --- |
| COMPONENT | CONCENTRATION/ML OF TOTAL CIRCUIT |
| BLOOD COLLECTION AND AUTO TRANSFUSION -750 ML | |
| Post autotransfusion yield | n/a |
| BLOOD RECONSTITUTION 260 ML | |
| Plasmalyte 200 ml | n/a |
| Albumin | 7.7 mg/ml |
| Heparin | 6.15 iu/ml |
| CIRCUIT PRIME 604 ML | |
| Transmedics priming solution 500 ml | n/a |
| Albumin | 7.7 mg/ml |
| Ciprofloxacin | 0.06 mg/ml |
| Cefazolin | 0.62 mg/ml |
| Adult Multi-V | 1 unit |
| Solumedrol | 0.15 mg/ml |
| Sodium Bicarbonate | 0.012 mEq/ml |
| CORRECTIVE MEDICATIONS 12 ML | |
| Calcium Gluconate | 0.37 mg/ml |
| Dextrose | 0.615 mg/ml |
| Sodium Bicarbonate | 0.003 mEq/ml |

After 2 hours of perfusion on the OCS device, the heart was re-arrested with del-Nido crystalloid solution. The heart was then implanted in a blood type compatible recipient animal in a heterotopic fashion (Kadner, A., Chen, R. H. & Adams, D. H. Heterotopic heart transplantation: experimental development and clinical experience. *Eur J Cardiothorac Surg* 17, 474-481 (2000)). The pulmonary artery from the allograft was anastomosed in an end to side fashion to the infra-renal IVC, and the ascending aorta from the allograft anastomosed in a similar fashion to the infra-renal abdominal aorta. Recipient pigs were pre-treated with a 1000 mg solumedrol bolus followed by maintenance immunosuppression with prednisolone, cyclosporine, and imuran as described by Swindle et al. (Swindle, M. M. & Smith, A. C. *Swine in the Laboratory*. (2016)). The animals were assessed daily for vital signs and graft function via palpation of the beating heart and with echocardiography.

The allograft, native heart, and samples from other organs (liver, lungs, spleen, psoas muscle) were procured on day 5 post-transplant at the time of euthanasia. Prior to harvest, graft function was evaluated by echocardiography. The abdominal aorta and thoracic aorta were both cannulated, and both hearts were arrested simultaneously using del-Nido solution infusion. The tissues were explanted, sectioned, and flash frozen in liquid nitrogen for assessment of transgene DNA, enzymatic activity and protein expression.

Example 3: Assessment of Transgene Activity and Expression

Luciferase Assay

Tissue samples (500 mg) were pulverized using a mortar and pestle and incubated for 30 minutes in 500 ul of passive lysis buffer (Promega, Madison, WI), then centrifuged for 15 min at 1300 rpm. Protein concentration of the resulting supernatant was determined using the Pierce BCA protein assay kit and a biokinetics reader (EL-340; BioTek Instruments). Equivalent protein amounts of the supernatant were assessed for luciferase activity using the Luciferase Assay Reagent (ONE-Glo, Promega, WI) per the manufacturer's instruction. The light emission was measured using a Veritas luminometer (Turner Biosystems, Sunnyvale, CA).

Western Blotting

Flash frozen sections of tissue were homogenized at 4° C. in lysis buffer (0.1% Triton X-100, 25 mM Tris-HCl, 150 mM NaCl, pH 7.4, 5 mM EDTA, Pierce Protease Inhibitor Minitablet (Pierce, product #88665). Homogenates were assayed for protein concentration (BCA assay, Pierce) and equivalent amounts of protein were added to the gels (Tris-Glycine, 4-12% gradient, Invitrogen). Blots were blocked (5% nonfat milk in Tris buffered saline with Tween 20 (TBST)). Blots were then incubated with primary antibody (rabbit anti-firefly luciferase, Abcam product # ab21176). After washing, an anti-rabbit IgG secondary antibody conjugated to horse radish peroxidase was added (Invitrogen SA1-200). Blots were them developed using Enhanced Chemiluminescent Substrate (ECL) (ThermoFisher Scientific Pierce).

Immunostaining

Immunostaining of tissue sections was done using a primary Rabbit Anti-Firefly Luciferase antibody (Abcam product # ab21176) and a Donkey Anti-Rabbit IgG secondary conjugated to Alexa Fluor 594 (Abcam product # ab150076). 15-micron sections of the tissue were placed on slides and kept at −80° C. The slides were then washed using TBS plus 0.05% Triton X-100 buffer. Samples were blocked in 10% goat serum with 1% BSA. Primary antibody (12 hours at 4° C.) was used per manufacture's recommended dilution. After washing, the secondary antibody was added at the manufacture's recommended concentration for 1 hour at room temperature. Fluorescent imaging was done using a Leica SP5 confocal system.

Quantitative Real Time PCR (qPCR) Analysis qPCR was used to determine viral genome copies in allograft and control tissues. Tissue samples were acquired at the time of animal sacrifice and stored in liquid nitrogen until DNA isolation. Total DNA was isolated with a DNeasy Blood and Tissue Kit (Qiagen). DNA purity and concentration were assessed using a NanoDrop Spectrophotometer. qPCR was performed for the Luciferase gene using the iQ SYBR Green Supermix (Bio-Rad) and the CFX Connect Real-Time PCR Detection System (Bio-Rad, Hercules, CA) with 30 cycle amplification of 95 C for 10 seconds; 59.5 C for 10 seconds; 72 C for 30 seconds. A standard curve was generated using known concentrations of the CMV-Luc plasmid via serial 1:10 dilutions. Starting luciferase gene copy number was estimated for each of the samples and reported as viral copies per starting amount of total DNA isolated. The primers used for Luciferase template amplification were (Forward-5'-CTCACTGAGACTA-CATCAGC-3 (SEQ ID NO: 1), and Reverse-5'-TCCA-GATCCACAACCTTCGC-3 (SEQ ID NO: 2)).

Example 4: Impact of Ex Vivo Perfusion Components on Viral Vector Transduction This study examined the feasibility of using normothermic ex vivo perfusion as a delivery system to administer biologicals (such as viral vectors) to a donor heart prior to transplantation. There are many components of the ex vivo perfusion system and each of these might affect the viral transduction process. In order to evaluate the influence of the major components of the OCS on the transduction efficiency of an Adenoviral (Ad)-luciferase serotype 5 vector, a cell-based luciferase assay was utilized to assess the influence of biologicals and chemicals on viral vector transduction (Messina, E. L. et al. Adeno-associated viral vectors based on serotype 3b use components of the fibroblast growth factor receptor signaling complex for efficient transduction. *Hum Gene Ther* 23, 1031-1042, doi:10.1089/hum.2012.066 (2012)).

Figure 1B:
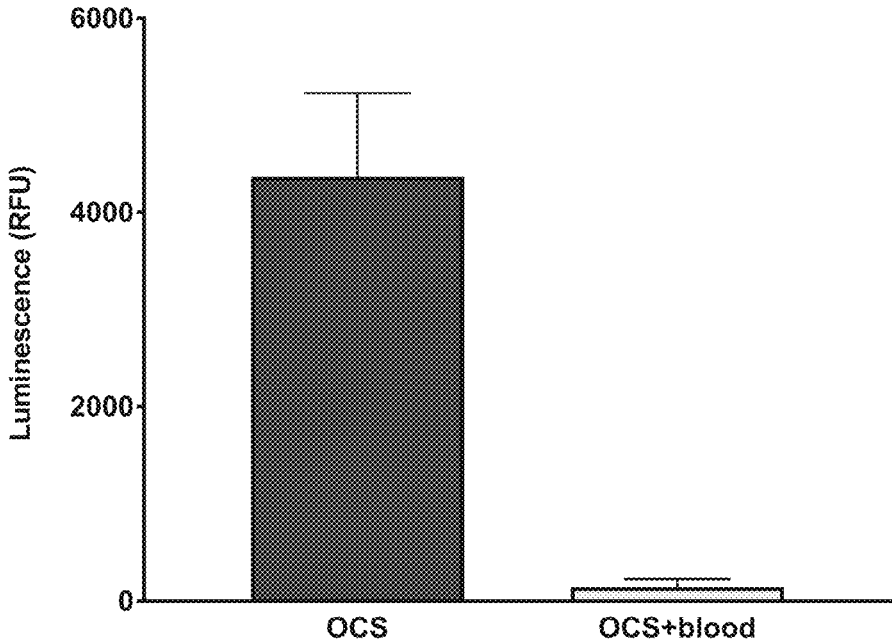

As can be seen in FIG. 1A, the perfusion solution did not interfere with the ability of the Ad luciferase vector to transduce HeLa cells at any concentration of solution tested. However, when the transduction experiments were performed in the presence of a perfusion solution/whole blood (porcine) mixture, an almost complete reduction in transduction was observed (FIG. 1B).

Figure 1C:
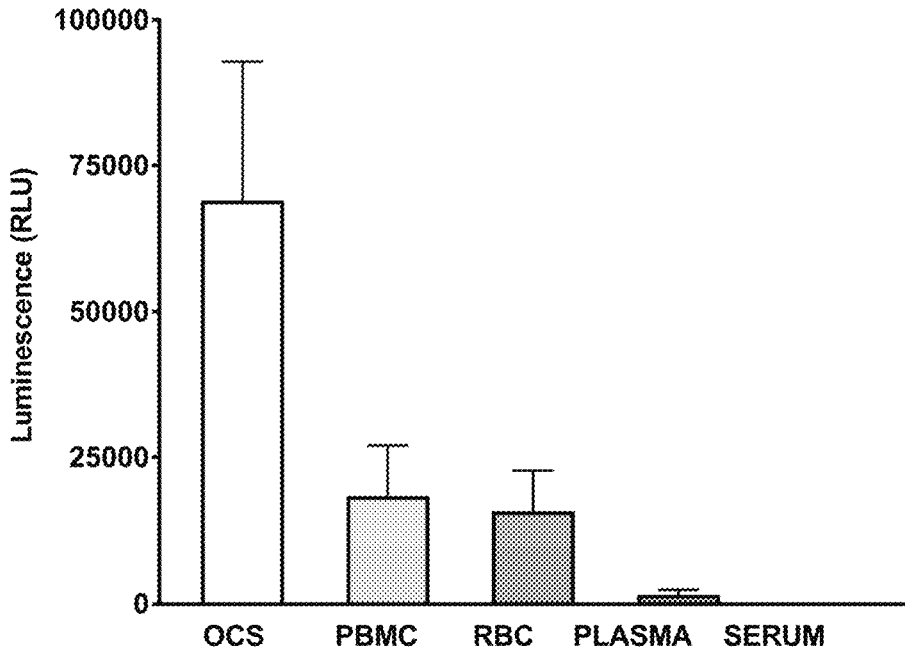

In order to determine which of the porcine blood components interfered with Ad vector transduction in the context of the perfusion solution, blood derivatives (Red Blood Cells (RBC), Peripheral Blood Mononuclear Cells (PBMC), serum, and plasma) were individually assessed in the cell-based assay. All of the blood components tested inhibited Ad transduction to some degree (FIG. 1C), with both the plasma and serum almost completely inhibiting transduction.

Neutralizing antibodies in the plasma and serum fractions of blood are known to limit the success of viral based gene delivery and are often exclusion criteria for clinical trials involving viral vectors (Harvey, B. G. et al. Variability of human systemic humoral immune responses to adenovirus gene transfer vectors administered to different organs. *J Virol* 73, 6729-6742 (1999)). The presence of pre-existing neutralizing antibodies in the pig provides an explanation for the observations in these experiments. To mitigate this issue, subsequent experiments used only the cellular fraction of centrifuged heparinized donor blood for the perfusate. Clinically, this blood centrifugation process, termed "Cell Saving," is commonly used to repurpose the blood that is lost during surgery and auto-transfuse concentrated red blood cells. This process should enable removal of antibodies (along with other serum proteins), thus generating a perfusate that better supports viral vector transduction. Once the blood is washed, it is important to re-establish the correct electrolyte balance and oncotic pressure (see Table 1).

Figure 1D:
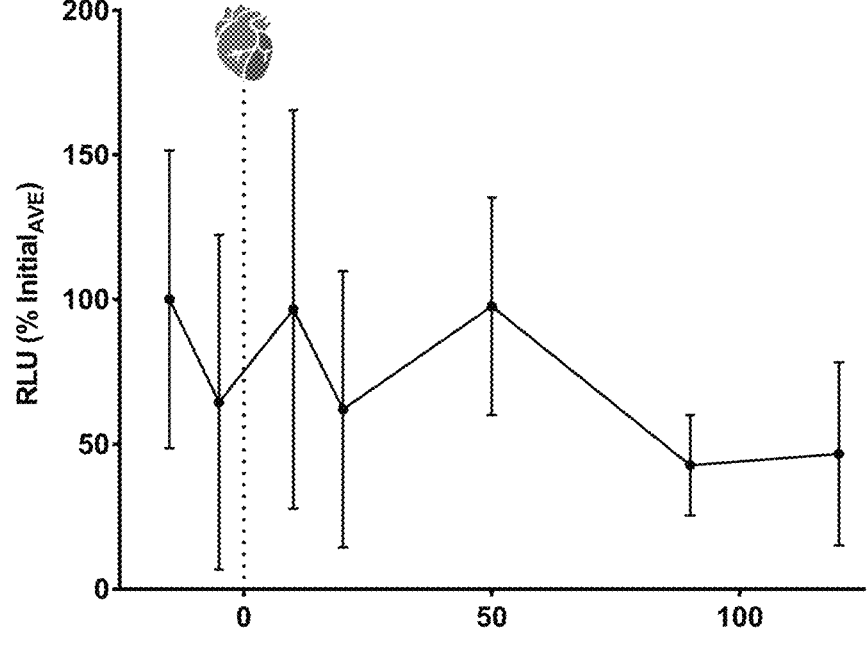

Indeed, the inhibitory influence of the plasma or serum was minimized when a donor heart was placed upon the circuit with a perfusate consisting of perfusion solution reconstituted with blood cells, which had been obtained following blood washing using a Cell Saver Device (see Table 1). Ad vector was added to the perfusion system and re-circulated for 2 hours. Perfusate from this experiment was obtained at various time points before and after the addition of the donor heart and perfusate samples were evaluated for transduction in the cell-based assay. As can be seen in FIG. 1D, the ability of the viral vector to transduce Hela cells was not appreciably affected at any time point in the presence of the fully assembled ex vivo perfusion device. Statistically insignificant reduction in transduction efficiency at the end of the perfusion period may represent the vector uptake onto components of the circuit or into the heart.

Example 5: Gene Delivery During Ex Vivo Perfusion and Heterotopic Heart Transplant A pig heterotopic transplant model was utilized (Kadner, A., Chen, R. H. & Adams, D. H. Heterotopic heart transplantation: experimental development and clinical experience. *Eur J Cardiothorac Surg* 17, 474-481 (2000)) as the pig heart is large enough to be placed on the clinical perfusion device and the pig donor provides adequate blood volume to prime the circuit. These similarities between pig and human hearts should allow for rapid clinical adoption. In addition, the heterotopic transplant model does not require the graft to support the systemic circulation, which allowed us to study gene expression originating from the viral vector, even if graft dysfunction occurred.

Figure 2:
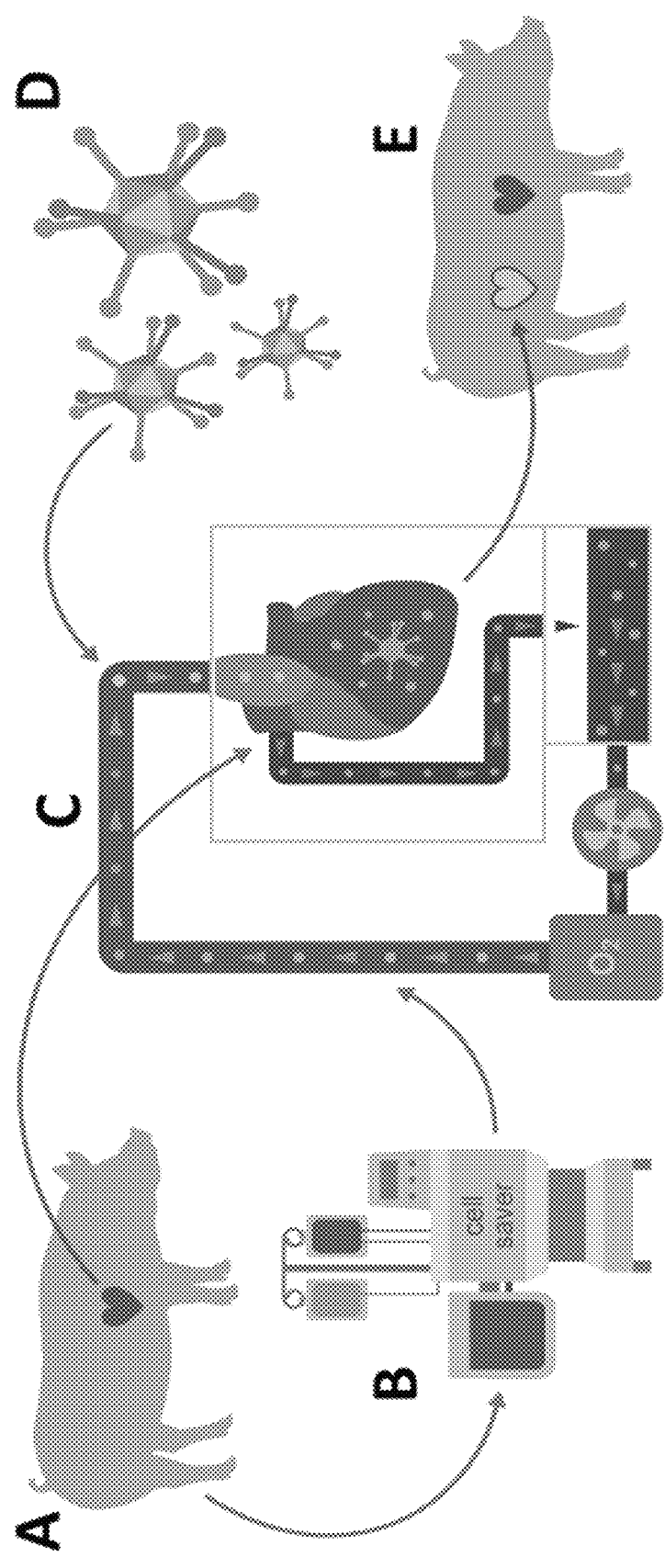
FIG. 2. Experimental Overview. Step A: Organ and blood donation. Step B: Washing of donor blood. Step C: Ex vivo perfusion using washed donor blood. Step D: Addition of viral vector. Step E: Heterotopic heart transplant.

The overall experimental strategy is depicted in FIG. 2. First, the donor pig provided both the donor heart and blood volume for the OCS circuit (FIG. 2, step A). The whole blood from the donor pig was washed using a cell saver/autotransfusion approach to isolate the red blood cells from the serum elements (FIG. 2, step B) and then reconstituted using components to match the osmotic pressures of whole blood (see Table 1). The washed and reconstituted blood was mixed with OCS solution and used to prime the ex vivo circuit (FIG. 2, step C). Then $5 \times 10^{13}$ particles of Ad-CMV luciferase were added directly to the circuit (FIG. 2, step D). The heart was then placed on the ex vivo perfusion device and perfused for 2 hours after which it was transplanted into the abdomen of the recipient animal (FIG. 2, step E).

Example 6: Evaluation of Transgene Expression Post-Transplant

Three separate transplant experiments were conducted successfully with no adverse events seen in the recipient animals. All allografts were viable at five days post-transplant but were not fully interrogated for rejection by histological examination. The overall transgene DNA copy number, levels of protein expression, protein activity, as well as the bio distribution of the firefly luciferase protein were evaluated in these three heart transplants 5 days post-transplant. The allograft and native heart were excised from the animals and regions of the heart (RV, LV, ventricular septum) were subdivided into sections. Each section was assessed for luciferase enzyme activity and summary data of all three hearts are provided in Table 2.

TABLE 2

| | | | | | |
|---|---|---|---|---|---|
| Luciferase expression levels from naïve heart, three native hearts, and three allografts. | | | | | |
| Heart Region | Naïve heart RLU/mg protein | Native heart (n = 3) RLU/mg protein | Allograft 1 RLU/mg protein | Allograft 2 RLU/mg protein | Allograft 3 RLU/mg protein |
| Left ventricle sections | | | | | |
| Atrioventricular junction | 104.4 ± 21.4 | 67.4 ± 49.9 | 1630.0 ± 368.4 | 186132.8 ± 4412.1 | 91204.0 ± 18571 |
| Middle | 104.4 ± 30.0 | 60.7 ± 36.8 | 3908.0 ± 382.8 | 145482.6 ± 782.1 | 659463.0 ± 9544.59 |
| Juxta apex | 131.1 ± 36.7 | 287.4 ± 185.1 | 28053.0 ± 594.2 | 643349.4 ± 6362.2 | 667541.2 ± 5044.4 |
| Apex | 115.5 ± 45.3 | 747.3 ± 853.2 | 14560.1 ± 1146.1 | 788750.4 ± 33528.2 | 1437765.5 ± 8713.1 |

TABLE 2-continued

| | | Native heart | | | |
|---|---|---|---|---|---|
| Heart Region | Naïve heart RLU/mg protein | (n = 3) RLU/mg protein | Allograft 1 RLU/mg protein | Allograft 2 RLU/mg protein | Allograft 3 RLU/mg protein |
| | | | Right ventricle sections | | |
| Atrioventricular junction | 771.1 ± 1049.7 | 80.5 ± 107.6 | 12226.9 ± 1065.4 | 12708147.5 ± 283221.4 | 316520.9 ± 18900.4 |
| Middle | 71.1 ± 33.5 | 43.3 ± 23.0 | 2293.4 ± 280.9 | 740159.9 ± 26207.5 | 2366458.6 ± 22373.2 |
| Juxta apex | 126.6 ± 33.3 | 81.3 ± 18.0 | 27987.2 ± 4801.6 | 2672829.0 ± 33050.2 | 392790.5 ± 6131.9 |
| Apex | 137.7 ± 36.7 | 456.7 ± 618.4 | 1994.4 ± 132.1 | 782733.2 ± 6536.0 | 9099456.5 ± 73751.5 |
| | | | Ventriclular septum sections | | |
| Atrioventricular junction | 186.6 ± 103.7 | 66.6 ± 51.5 | 13835.0 ± 749.4 | 635594.0 ± 13516.8 | 745212.5 ± 17625.5 |
| Middle | 122.2 ± 7.6 | 44.6 ± 51.1 | 8495.7 ± 278.6 | 163896.0 ± 2359.3 | 449768.9 ± 9206.1 |
| Juxta apex | 111.1 ± 10.1 | 187.6 ± 245.7 | 36349.7 ± 1094.9 | 2898714.2 ± 94065.9 | 1668397.2 ± 21115.1 |
| Apex | 148.8 ± 30.0 | 62.3 ± 61.2 | 2998.3 ± 435.3 | 93257.7 ± 2506.8 | 2434775.2 ± 58712.1 |

Data is presented as mean ± SD
(RLU = relative light units)

The luciferase protein activity in the donor heart appeared robust across all areas of the myocardium as well as in the coronary arteries. The recombinant adenoviral vectors efficiently transduced a large cardiac allograft during a relative short period of ex vivo perfusion. At a minimum luciferase activity was 10 times that of the recipient's native heart, and at a maximum, it was 20,000 fold higher than the native heart. While all areas of the heart displayed high luciferase activity, this luciferase activity was not evenly distributed.

Figure 3A:
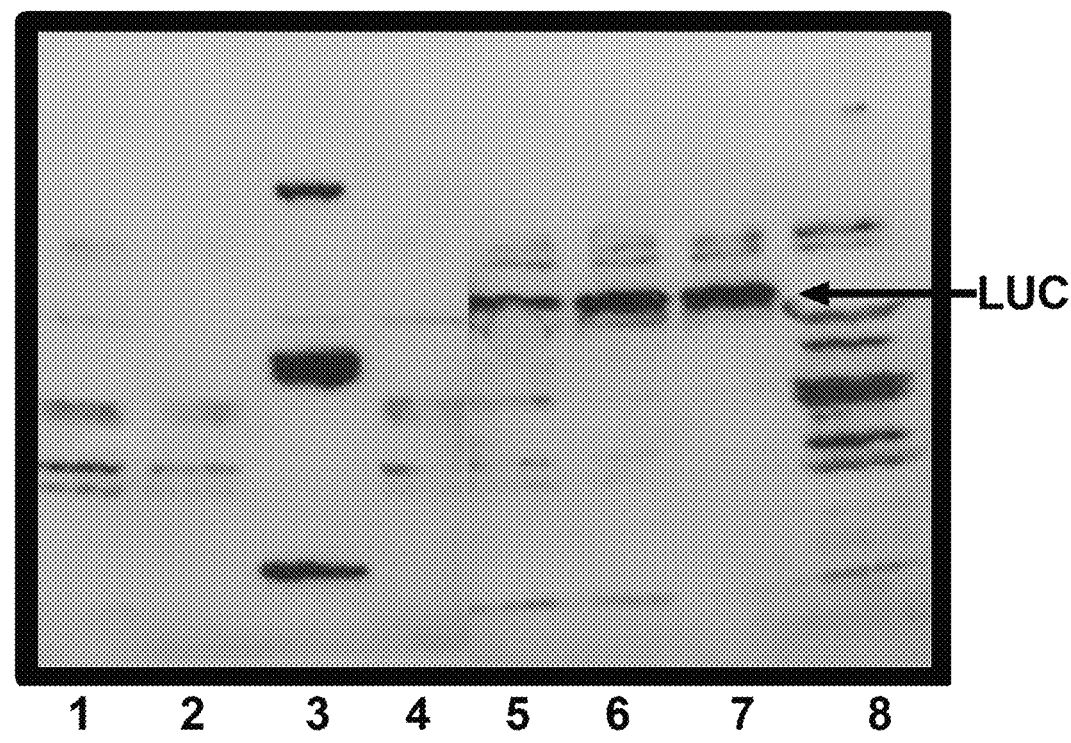
FIGS. 3A-3B. Luciferase protein expression in trans- planted heart.
Figure 3B:
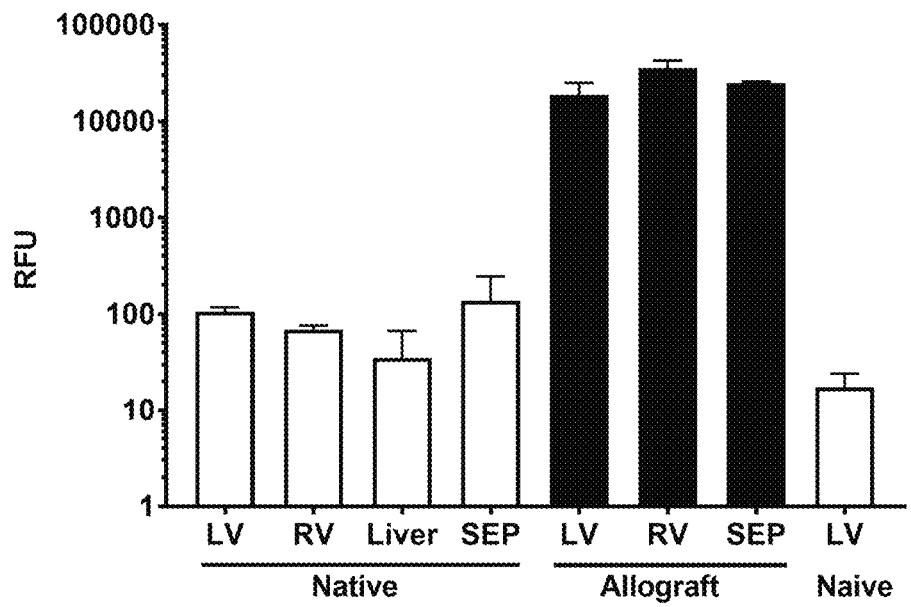

In addition to the quantitation of luciferase activity, protein lysates from all animals were examined for evidence of luciferase protein in regions of the heart and in various organs. As can be seen in FIG. 3A, the firefly luciferase protein of 62 kDa was present at high levels in lysates from the LV, RV, and interventricular septum of the allograft (lanes 5-7) but was not observed in native heart LV, RV, or septum (lanes 1, 2, or 4). A protein of 62 kDa corresponding to the luciferase protein was not observed in LV lysates from a naïve pig, i.e. a control pig that did not receive a transplant and that had not been administered the Ad viral vector (lane 8). Luciferase activity corresponding to each of the tissues in FIG. 3A is shown in FIG. 3B. Importantly, luciferase activity was only evident in tissues that expressed the 62 kDa protein (allograft tissues only). Luciferase activity and luciferase protein was not observed in native tissues or naïve tissue.

Transgene expression at the protein level was further verified using immunostaining. There was a high abundance of the luciferase protein in virtually all myocardium examined, with no staining seen in the control native myocardium. Furthermore, staining of the LAD demonstrated excellent luciferase staining in all layers of the artery.

Luciferase activity in all other organs of the recipient was similar to background suggesting minimal washout of the vector to remote tissue (Table 3).

TABLE 3

Luciferase activity levels measured in organs from recipient.

| TISSUE | RLU/MG PROTEIN |
|---|---|
| Liver | 6.5 ± 3.0 |
| Lung | 6.4 ± 6.9 |

TABLE 3-continued

Luciferase activity levels measured in organs from recipient.

| TISSUE | RLU/MG PROTEIN |
|---|---|
| Spleen | 11.2 ± 9.7 |
| Psoas muscle | 7.9 ± 2.0 |
| Aorta adjacent to graft | 10.2 ± 11.1 |
| IVC adjacent to graft | 20.9 ± 12.6 |

(RLU = relative light units)

While it is difficult to fully compare given many differences in experimental setup, the degree of transgene expression in the present study appears to exceed that achieved with other experimental methods of cardiac gene delivery such as catheter directed intracoronary injection or direct myocardial injection.

Figure 4:
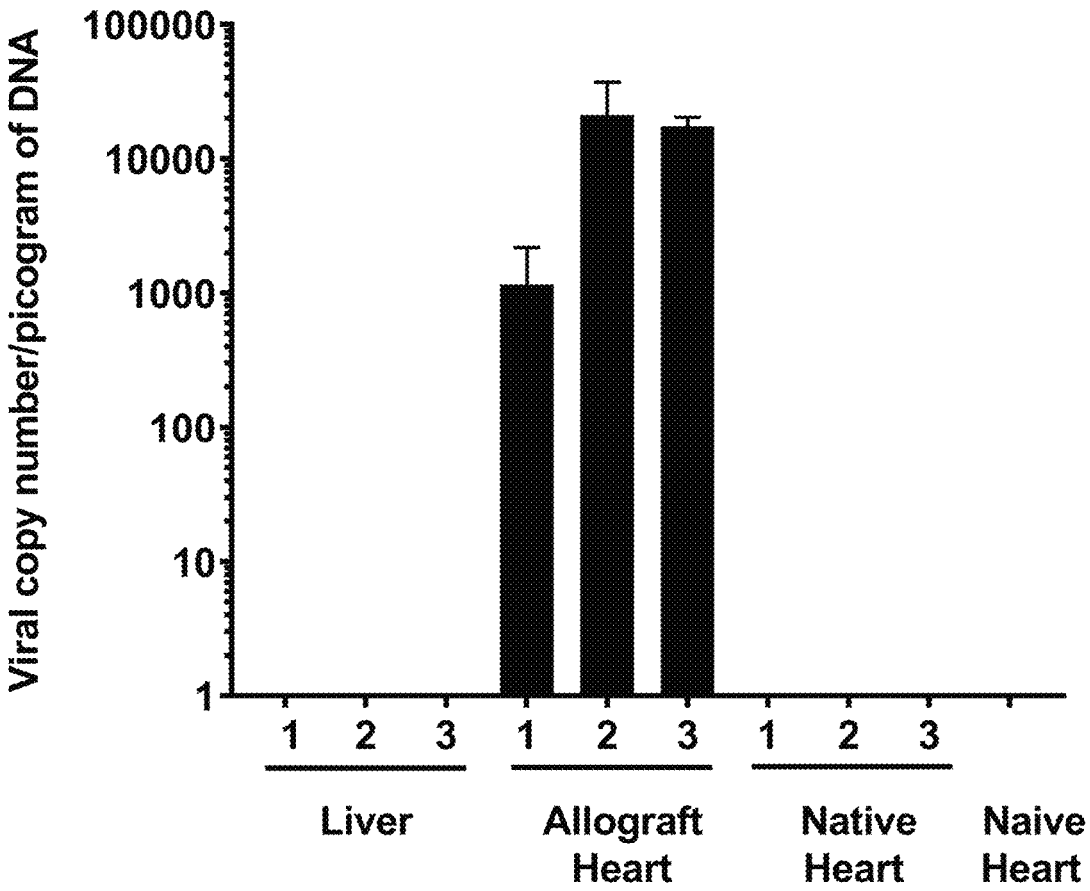
FIG. 4. Quantitative real time PCR assessment of trans- gene copy number present per picogram of DNA isolated from liver, heart allograft, naïve and native hearts. (n=3, except naïve heart n=1).

Finally, the concentration of viral vector DNA in the allografts, native heart and livers of the recipient animals was examined by quantitative real time PCR using luciferase specific primers. High transgene copy number was confirmed in all three allografts, while recipient native heart and livers displayed no signal (FIG. 4). These findings of vector copy number mirror those of the luciferase gene expression and further supporting limited spread of vector from the transplanted organ.

Accordingly, the above findings suggest that viral vector delivery of therapeutic transgenes during ex vivo perfusion may be an efficient and safe strategy to transduce large allografts.

Example 7: Long-Term Transgene Expression Post-Transplant with an AAV Vector

A luciferase assay was conducted using the same experimental protocol as for the Ad vector as presented in the examples above, but for using Yucatan pigs (rather than Yorkshire pigs), and but for using an AAV vector (SASTG). Luciferase expression results after 30 days are presented in Table 4. 8 ug of protein was used for all specimens for each of 3 triplicates.

17 18

TABLE 4

Luciferase activity levels measured 30 days after transplant.

| Heart Region | Allograft RLU/mg protein | Native Heart RLU/mg protein |
|---|---|---|
| LV base | 41,819 | Undetectable |
| LV mid (superior) | 44,939 | Undetectable |
| LV mid (inferior) | 104,115 | Undetectable |
| LV apex | 111,221 | Undetectable |

(RLU = relative light units)

We claim:

1. A method of administering a therapeutic agent to a human donor organ, the method comprising:

maintaining the human donor organ under normothermic ex vivo perfusion conditions prior to transplant into a human subject in need of an organ transplant, wherein the therapeutic agent comprises a viral vector comprising a transgene, wherein the transgene is under control of a promoter and encodes a protein that mitigates graft dysfunction or allograft vasculopathy;

wherein the human donor organ is allogeneic or autologous to the human subject;

wherein the therapeutic agent is circulated in the perfusion conditions comprising a perfusion solution mixture comprising washed red blood cells substantially free of plasma and serum reconstituted with isotonic non-pyrogenic intravenous (IV) crystalloid solution, albumin, and heparin, and a priming solution comprising albumin, ciprofloxacin, cefazolin, adult multivitamins, sodium bicarbonate, methylprednisolone, calcium gluconate, and dextrose; and wherein the viral vector is an adeno-associated viral vector.

2. The method of claim 1 wherein the human donor organ is a heart and the subject needs a donor heart.

3. The method of claim 1 wherein the human donor organ is a kidney and the subject needs a donor kidney, wherein the donor organ is a liver and the subject needs a donor liver, or wherein the human donor organ is a lung and the subject needs a donor lung.

4. The method of claim 1 wherein the ex vivo perfusion conditions are maintained using a Langendorff perfusion system or a warm blood perfusion system.

5. The method of claim 1 wherein circulating the therapeutic agent through the human donor organ while maintaining the perfusion conditions comprises:

a. harvesting the human donor organ and blood from the human donor;

b. priming the ex vivo perfusion circuit with the perfusion solution mixture;

c. adding the therapeutic agent to the ex vivo perfusion circuit and placing the human donor organ on the ex vivo perfusion device; and d. perfusing the human donor organ.

6. The method of claim 5 wherein perfusing the human donor organ comprises perfusion for 2 or more hours.

7. The method of claim 1 further comprising subsequently transplanting the human donor organ into the human subject in need thereof.

8. A method of modifying a human donor organ prior to transplantation, the method comprising:

maintaining the human donor organ under normothermic ex vivo perfusion conditions and administering a viral vector encoding a transgene to the human donor organ and circulating the viral vector through the human donor organ;

wherein the transgene is under control of a promoter and encodes a protein that mitigates graft dysfunction or allograft vasculopathy;

wherein the viral vector is circulated in the perfusion conditions comprising red blood cells substantially free of plasma and serum reconstituted with isotonic non-pyrogenic IV crystalloid solution, albumin, and heparin, and a priming solution comprising albumin, ciprofloxacin, cefazolin, adult multivitamins, sodium bicarbonate, methylprednisolone, calcium gluconate, and dextrose; and wherein the viral vector is an adeno-associated viral vector.

9. The method of claim 8 wherein circulating the viral vector through the human donor organ comprises circulation for 2 or more hours.

10. A method of treating organ failure in a subject, the method comprising:

transplanting a human donor organ into a human subject in need thereof, wherein a viral vector encoding a transgene has been administered to a human donor organ prior to transplantation by a method comprising maintaining the human donor organ under normothermic ex vivo perfusion conditions prior to the transplantation and circulating the viral vector through the human donor organ in the perfusion conditions; wherein the transgene is under control of a promoter and expresses a protein that mitigates graft dysfunction or allograft vasculopathy; wherein the human donor organ is allogeneic or autologous to the human subject; wherein the viral vector is circulated in a perfusion solution mixture comprising washed red blood cells substantially free of plasma and serum reconstituted with isotonic non-pyrogenic IV crystalloid solution, albumin, and heparin, and a priming solution comprising albumin, ciprofloxacin, cefazolin, adult multivitamins, sodium bicarbonate, methylprednisolone, calcium gluconate, and dextrose; and wherein the viral vector is an adeno-associated viral vector.

11. The method of claim 10 wherein the subject in need thereof has organ failure, wherein the organ failure is heart failure, and wherein the human donor organ is a donor heart.

12. The method of claim 10 wherein circulating the viral vector through the human donor organ comprises circulation for 2 or more hours.

\* \* \* \* \*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Forward Primer

<400> SEQUENCE: 1
ctcactgaga ctacatcagc                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse

<400> SEQUENCE: 2
tccagatcca caaccttcgc                                               20
```